United States Patent [19]

MacMurray

[11] 3,967,953

[45] *July 6, 1976

[54] ROSE GROWTH STIMULATION

[75] Inventor: Robert R. MacMurray, Bloomsburg, Pa.

[73] Assignee: American Agtech, Inc., Bloomsburg, Pa.

[ * ] Notice: The portion of the term of this patent subsequent to Oct. 10, 1989, has been disclaimed.

[22] Filed: Nov. 25, 1974

[21] Appl. No.: 526,819

Related U.S. Application Data

[63] Continuation-in-part of Ser. No. 186,508, Oct. 4, 1971, Pat. No. 3,861,901, which is a continuation-in-part of Ser. No. 3,697,253, April 11, 1969.

[52] U.S. Cl. .................................. 71/97; 71/117; 71/121
[51] Int. Cl.² ........................................ A01N 9/20
[58] Field of Search ..................... 71/97, 121, 117

[56] References Cited
UNITED STATES PATENTS
3,257,190   6/1966   Soper .................................. 71/121
3,697,253  10/1972   MacMurray ........................ 71/97

Primary Examiner—Elbert L. Roberts
Assistant Examiner—Catherine W. Mills
Attorney, Agent, or Firm—Max R. Millman

[57] ABSTRACT

A method of stimulating the growth of roses, particularly in greenhouses, by applying to the rose bushes N,N-di-n-propyl-4-trifluoromethyl-2,6-dinitroaniline, known generally as trifluralin, in combination with 2,4-dichlorophenoxyacetic acid (2,4-D). The method also comprises applying trifluralin and 2,4-D in combination with cacodylic acid.

6 Claims, No Drawings

ROSE GROWTH STIMULATION

This invention relates to plant growth regulation, particularly rose growth stimulation, and is a continuation-in-part of my copending application Ser. No. 186,508 filed Oct. 4, 1971 now U.S. Pat. No. 3,861,901 which is, in turn, a continuation-in-part of my U.S. Pat. No. 3,697,253 filed Apr. 11, 1969.

Said parent U.S. Pat. No. 3,697,253 discloses that the herbicide N,N-di-n-propyl-4-trifluoromethyl-2,6-dinitroaniline, known generally as trifluralin, stimulated the growth of herbaceous and woody stemmed plants and increased crop yield when applied thereto in concentrations and amounts sufficient to effect growth stimulation. Said patent also discloses plant growth stimulation when trifluralin is combined with cacodylic acid and/or 2,4-dichlorophenoxyacetic acid (2,4-D) and/or 2,4,5-trichlorophenoxyacetic acid (2,4,5-T).

Said patent application Ser. No. 186,508 discloses that the growth of peppers and Douglas Firs are stimulated by applying thereto trifluralin or a chlorinated phenoxyacetic acid and that the growth of soybean and alfalfa plants are stimulated by applying thereto trifluralin and 2,4-dichlorophenoxyethyl sulfate, in concentrations and amounts sufficient to effect growth stimulation.

The instant invention is based on the discovery that the growth of roses, particularly in greenhouses, is stimulated and increased by the application to the rose bushes of compositions containing as active ingredients trifluralin in combination with 2,4-D in concentrations and amounts sufficient to effect growth stimulation of the roses.

Another object of the invention is to provide a method of stimulating and increasing the growth of roses by applying directly to the rosebushes in a concentration and amount sufficient to effect such stimulation a composition comprising trifluralin, 2,4-D and cacodylic acid as the active ingredients.

These and other objects of the invention will become more apparent as the following description proceeds, in which as in the parent U.S. Pat. No. 3,697,253, trifluralin is denoted as Compound A, cacodylic acid and its salts as Compound B and 2,4-D and its salts as Compound C.

The following is an illustrative but nonlimitative example of the instant invention and results obtained thereby.

EXAMPLE

A solution comprised by weight of 40% butanol, 40% Tween No. 20 (polyoxyethylene sorbitan monooleate) and 20% water is made up as a vehicle for the active ingredients, into which is dissolved 1.5% by weight of trifluralin, Compound A, and 0.5% by weight of 2,4-D, Compound C, as the acid, to form concentrate AC. 10 ml of such concentrate AC when dissolved in a gallon of water results in a concentration of 40.50 ppm trifluralin and 13.50 ppm 2,4-D.

Similarly, into the same butanol-Tween No. 20 water solution is dissolved 1.4% by weight of trifluralin, compound A, 4.6% by weight of cacodylic acid, Compound B, as the monosodium salt and 1.0% by weight of 2,4-D, Compound C as the acid to form concentrate ABC. 10 ml of such concentrate ABC when dissolved in a gallon of water results in a concentration of 39.50 ppm trifluralin, 130.00 ppm cacodylic acid and 28.30 ppm 2,4-D.

The active compounds were applied as sprays to drip off at various concentrations and amounts to rosebush plots in a commercial greenhouse which was conventionally maintained at a relative humidity of 20–95% and temperatures between 60°–75°F using highly organic soil, containing soil, peat moss, pearlite and peanut hulls. The spray plots and a control plot, all of equal size, were marked off and labelled in a large bed of Golden Wave roses. Buffer plots of equal size lay between each selected spray plot. Spray plots No. 1–5 were treated with compositions containing compounds A and C, spray plots No. 6–8 with compositions containing compounds A, B and C and plot No. 9 served as the control.

The sprays were applied to the rosebushes in accordance with the following Table.

Table 1

| Sprays Containing Compounds A and C | | | |
|---|---|---|---|
| AC MI Conc/Gal H$_2$O | Plot Applied To | Conc(ppm) A | C |
| 0.8 | 1 | 3.24 | 1.06 |
| 1.6 | 2 | 6.48 | 2.16 |
| 2.4 | 3 | 9.72 | 3.24 |
| 3.2 | 4 | 12.96 | 4.32 |
| 4.0 | 5 | 16.20 | 5.40 |

Table 2

| Sprays Containing Compounds A, B and C | | | | |
|---|---|---|---|---|
| ABC MI Conc/Gal H$_2$O | Plot Applied To | Conc(ppm) A | B | C |
| 2.5 | 6 | 9.88 | 32.5 | 7.08 |
| 5.0 | 7 | 19.76 | 65.0 | 14.16 |
| 7.5 | 8 | 29.64 | 97.5 | 21.24 |

The plots were each sprayed once to drip off on a particular Friday as a starting date. In addition to the permanent labels for each plot, weekly tags were attached to each of the nine plots. Every day, roses were cut from each such plot, and the number so cut recorded on the weekly tag which also bore the starting date of that seven-day week and the plot number. These tags were collected every Friday and tallied and recorded, after being replaced with a new weekly tag. The results are shown in Table 3.

Table 3

| Record of Golden Wave Rose Production, At A Commercial Greenhouse, Over An 18 Week Period | | | | | | | | | |
|---|---|---|---|---|---|---|---|---|---|
| Spray Plot No. | 1 | 2 | 3 | 4 | 5 | 6 | 7 | 8 | 9 |
| 1st Week | 16 | 9 | 10 | 8 | 8 | 14 | 3 | 6 | 9 |
| 2nd Week | 33 | 11 | 24 | 22 | 17 | 14 | 20 | 18 | 11 |
| 3rd Week | 2 | 12 | 2 | 7 | 4 | 6 | 7 | 16 | 2 |
| 4th Week | 1 | 0 | 0 | 0 | 0 | 0 | 0 | 1 | 0 |
| 5th Week | 0 | 0 | 0 | 0 | 0 | 0 | 0 | 0 | 0 |
| 6th Week | 0 | 0 | 0 | 0 | 0 | 0 | 0 | 0 | 0 |
| 7th Week | 2 | 4 | 5 | 0 | 0 | 2 | 0 | 0 | 3 |
| 8th Week | 16 | 10 | 8 | 8 | 17 | 10 | 2 | 5 | 11 |

Table 3-continued

Record of Golden Wave Rose Production,
At A Commercial Greenhouse, Over An 18 Week Period

| Spray Plot No. | 1 | 2 | 3 | 4 | 5 | 6 | 7 | 8 | 9 |
|---|---|---|---|---|---|---|---|---|---|
| 9th Week | 11 | 6 | 8 | 5 | 4 | 4 | 5 | 6 | 3 |
| 10th Week | 3 | 6 | 4 | 5 | 2 | 4 | 3 | 6 | 3 |
| 11th Week | 0 | 2 | 1 | 1 | 1 | 0 | 1 | 2 | 3 |
| 12th Week | 0 | 1 | 0 | 0 | 0 | 0 | 2 | 2 | 0 |
| 13th Week | 0 | 1 | 1 | 0 | 0 | 0 | 1 | 0 | 1 |
| 14th Week | 0 | 1 | 1 | 0 | 2 | 0 | 0 | 0 | 0 |
| 15th Week | 4 | 4 | 9 | 2 | 7 | 1 | 2 | 2 | 2 |
| 16th Week | 14 | 12 | 8 | 11 | 5 | 9 | 8 | 5 | 4 |
| 17th Week | 0 | 1 | 1 | 0 | 1 | 0 | 0 | 5 | 0 |
| 18th Week | 2 | 3 | 3 | 1 | 2 | 1 | 3 | 7 | 1 |
| TOTAL | 104 | 83 | 85 | 60 | 70 | 65 | 57 | 81 | 53 |
| % of Control | 196% | 137.7% | 160% | 113% | 132% | 122.6% | 107.5% | 150.9% | 100% |

In Table 3, the entries represent the total roses cut from the rosebushes for the prior week. Spray plots 1–5 were treated with compositions containing compounds A and C, plots 6–8 with compositions containing compounds A, B and C and plot 9 was the control.

In view of the leveling off effect of the spray solutions of the active ingredients at the 16th and 17th weeks, it is desirable that the rosebushes be resprayed with the growth stimulant compositions every 3 ½ to 4 months for optimum results.

The synergistic stimulation effect of the combination of trifluralin and 2,4-D on flowering plants is disclosed in my parent U.S. Pat. No. 3,697,253 in col. 18, Tables 11-A, 12-A and 14-A.

While preferred embodiments of the invention are described herein, it will be understood that skilled artisans may make variations without departing from the spirit of the invention. Thus, the rate of growth stimulation of some rose species other than Golden Wave may vary as to optimal level of treatment. Additionally, the water soluble salts of 2,4-D and cacodylic acid, such as the sodium salts as well as the acids themselves, may be used as the active ingredients and come within the purview of the invention.

What is claimed is:

1. A method of stimulating the growth of roses comprising applying thereto a composition including N,N-di-n-propyl-4-trifluoromethyl-2,6-dinitroaniline and 2,4-dichlorophenoxyacetic acid or salt thereof as active ingredients in a combined concentration and amount sufficient to stimulate growth of the roses.

2. The method of claim 1 wherein the composition is applied to the rosebushes to drip off under greenhouse conditions of 20–95% relative humidity and a temperature of 60°–75°F.

3. The method of claim 1 wherein the composition is applied to the rosebushes to drip off, said composition including about 3.2 to 16.2 ppm N,N-di-n-propyl-4-trifluoromethyl-2,6-dinitroaniline and 1.1 to 5.4 ppm 2,4-dichlorophenoxyacetic acid or salt thereof.

4. The method of claim 1 and cacodylic acid or a salt thereof as an additional active ingredient, the active ingredients being applied in a concentration and amount sufficient to stimulate growth of the roses.

5. The method of claim 4 wherein the composition is applied to the rosebushes to drip off under greenhouse conditions of 20–95% relative humidity and a temperature of 60°–75°F.

6. The method of claim 4 wherein the composition is applied to the rosebushes to drip off, said composition including about 9.9 to 29.6 ppm N,N-di-n-propyl-4-trifluoromethyl-2,6-dinitroaniline, 32.5 to 97.5 ppm cacodylic acid or salt thereof and 7.1 to 21.2 ppm 2,4-dichlorophenoxyacetic acid or salt thereof.

* * * * *